(12) United States Patent
Inana et al.

(10) Patent No.: US 8,474,303 B2
(45) Date of Patent: Jul. 2, 2013

(54) CHROMATOGRAPHIC MEASUREMENT APPARATUS

(75) Inventors: Katsuya Inana, Ashigarakami-gun (JP);
Tomonori Nishio, Ashigarakami-gun (JP); Junichi Katada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 299 days.

(21) Appl. No.: 12/895,003

(22) Filed: Sep. 30, 2010

(65) Prior Publication Data
US 2011/0072885 A1 Mar. 31, 2011

(30) Foreign Application Priority Data
Sep. 30, 2009 (JP) ................... 2009-226010

(51) Int. Cl.
*G01N 30/02* (2006.01)
(52) U.S. Cl.
USPC .......................................... 73/23.4; 73/23.35
(58) Field of Classification Search
USPC ............ 73/23.35, 23.4; 422/82.05; 435/287.1
See application file for complete search history.

(56) References Cited

U.S. PATENT DOCUMENTS
2003/0003522 A1 1/2003 Goldman
2005/0036915 A1* 2/2005 Yamauchi ............. 422/82.05
2005/0191210 A1* 9/2005 Mori et al. ............. 422/56
2006/0292650 A1 12/2006 Braig et al.
2008/0166821 A1 7/2008 Oyamada et al.

FOREIGN PATENT DOCUMENTS
| | | |
|---|---|---|
| EP | 2065706 A2 | 6/2009 |
| JP | 2009-133813 A | 6/2009 |
| JP | 2009-156612 A | 7/2009 |
| WO | 2008065474 A1 | 6/2008 |

OTHER PUBLICATIONS

Office Action dated Feb. 17, 2012, in corresponding European Patent Application 10182250.0.
European Search Report for EP 10 18 2250, issued Jun. 7, 2011.

* cited by examiner

*Primary Examiner* — Hezron E Williams
*Assistant Examiner* — David Z Huang
(74) *Attorney, Agent, or Firm* — Sughrue Mion, PLLC

(57) ABSTRACT

A chromatographic measurement apparatus for measuring a color development state of an insoluble carrier with a sample solution and a label solution developed thereon to test a test article, the insoluble carrier including a test detection area where a material that binds specifically to a test article is immobilized and a control detection area used for determining an end of measurement. The chromatographic measurement apparatus includes: a determining unit for carrying out determination of validity and determination of necessity of amplification of a test result of the test article; and an amplifying unit for amplifying the color development state according to the result of the determination of necessity of amplification by the determining unit. The amplification is carried out only when it is determined that amplification is necessary.

16 Claims, 11 Drawing Sheets

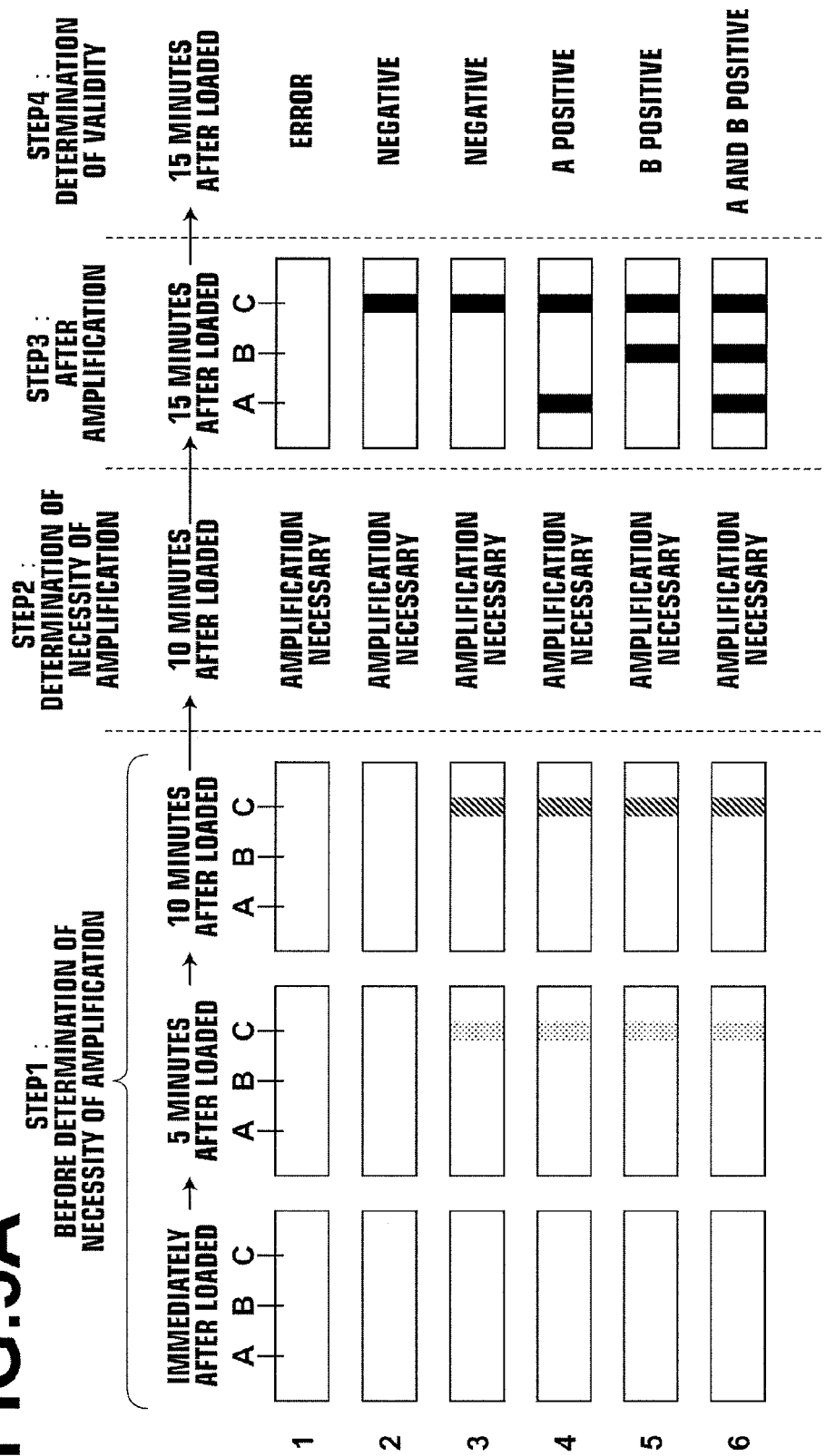

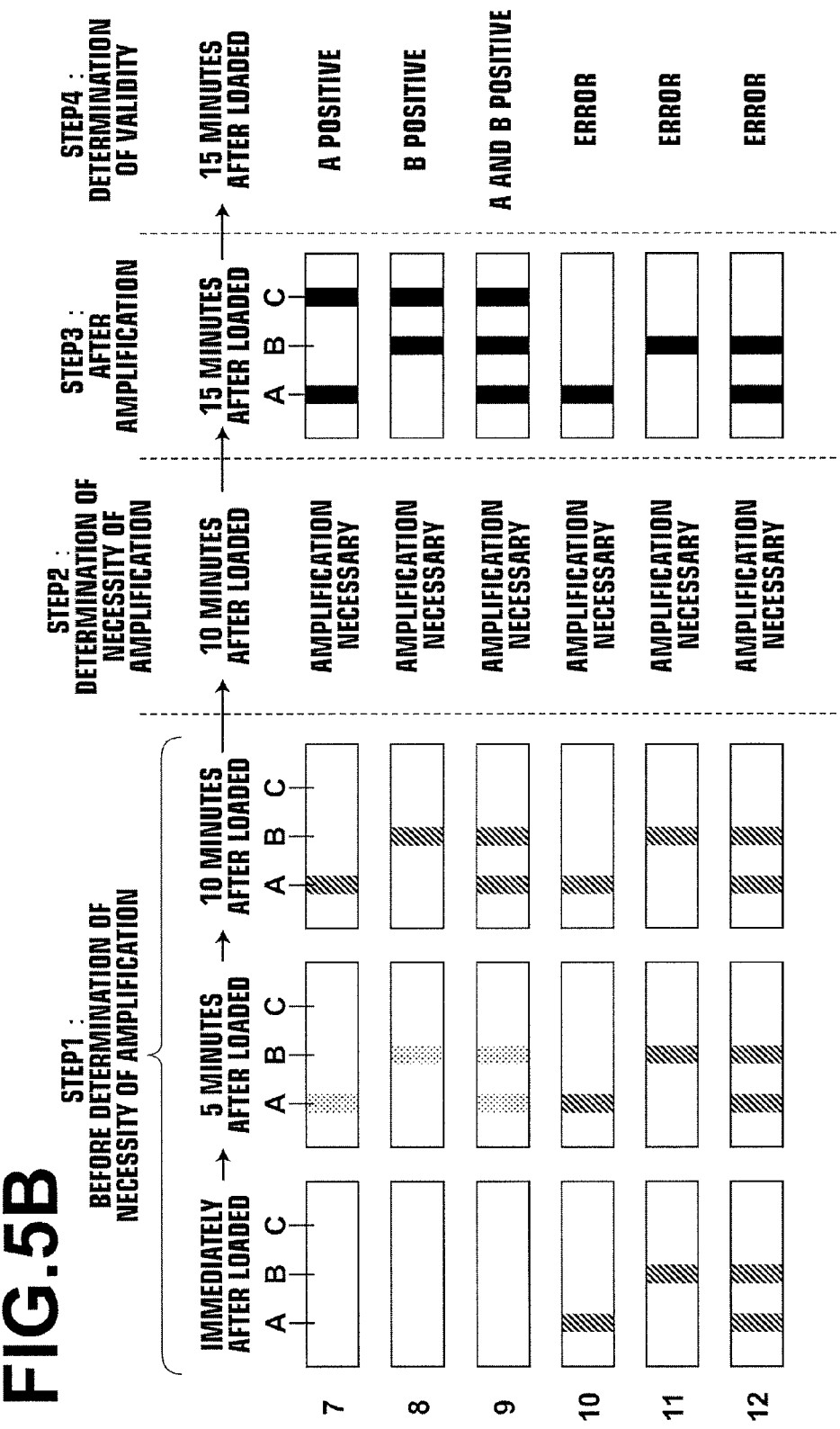

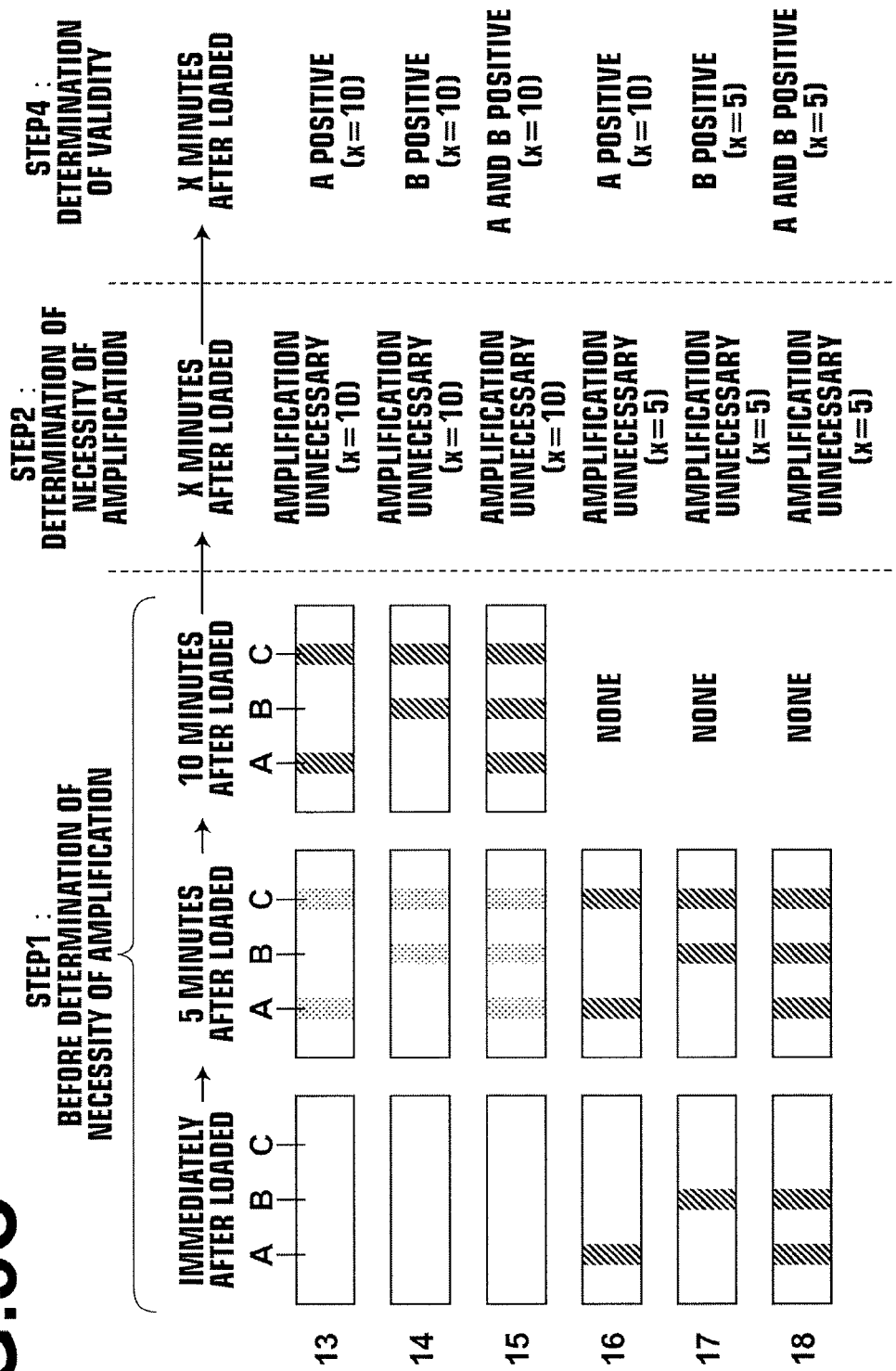

EXAMPLE 2 OF "ERROR" DETERMINATION: WHERE AMPLIFICATION WAS PARTIALLY UNSUCCESSFUL

EXAMPLE 3 OF "ERROR" DETERMINATION: WHERE AMPLIFICATION WAS UNSUCCESSFUL

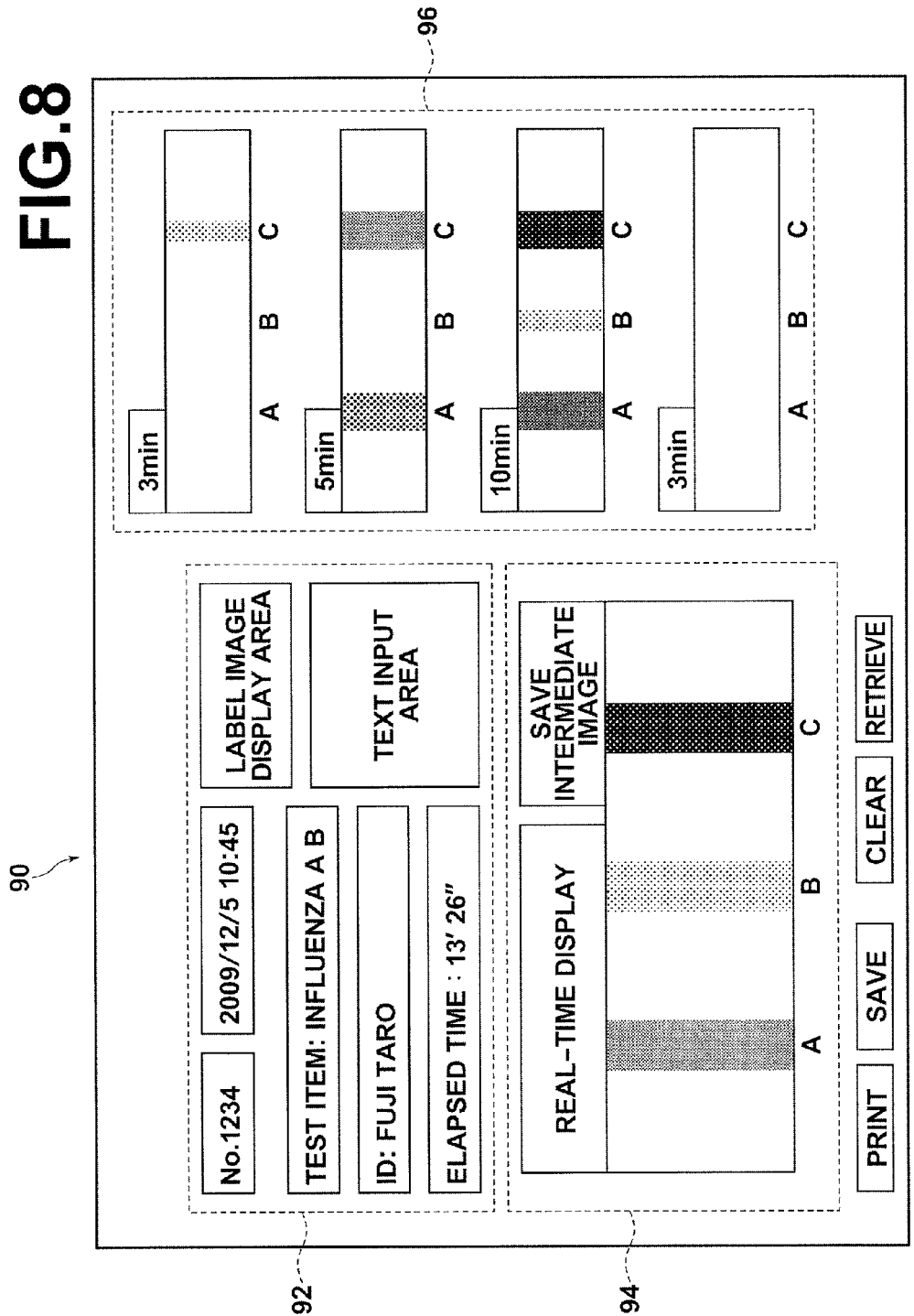

CHROMATOGRAPHIC MEASUREMENT APPARATUS

BACKGROUND OF THE INVENTION

1. Field of the Invention

The present invention relates to a chromatographic measurement apparatus that carries out measurement of an assay device using chromatography. In particular, the invention relates to a chromatographic measurement apparatus that tests a test article by measuring color development states of a test line, where a material that binds specifically to the test article is immobilized, and of a control line for determining the end of the measurement.

2. Description of the Related Art

In recent years, many assay devices have been developed, which are used to test a test article in simple and quick manner using an assay method, such as immunological measurement, where a sample (sample solution), which may possibly contain the test article, it fed onto a carrier. Now, various assay devices for testing extracorporeal diagnostic agents, toxic substances, etc., are commercially available. An example of such devices is one disclosed in U.S. Patent Application Publication No. 20080166821 (hereinafter, Patent Document 1), which uses immuno-chromatography. In the case where a device using immuno-chromatography is used, determination/measurement can be achieved in a simple manner without requiring a heavy equipment or machine, and the result of measurement can be obtained by putting the sample solution on the carrier and then leaving the carrier with the sample solution for as short as about 5 to 10 minutes, for example. Therefore, measurement techniques using an assay method, such as immunological measurement, are widely used as highly-specific, simple and quick measurement techniques in many situations, such as a clinical test at a hospital, a sample test at a laboratory, etc.

On the other hand, as a measurement apparatus for POCT (Point of Care Testing) for use at medical care sites, such as a doctor's office or a clinic, or at home, an immuno-chromatographic measurement apparatus (immuno-chromato-reader) is used for carrying out a test in a simple manner without need of a clinical test specialist. The immuno-chromatographic measurement apparatus allows highly sensitive measurement of a color development state of a reagent of a loaded device, and allows highly sensitive and highly reliable testing of the device even when the device is in a low color development state which is difficult to be observed and determined visually.

However, in order to carry out the test appropriately, it is necessary to wait for a reaction completion time (a time taken for the color development state of the test line to be visually observable after the sample solution is put on the device), which depends on the reagent (a material that binds specifically to the test article and being immobilized on the test line), after the sample solution is put on the device. This forces the user to measure the time after the sample solution is put on the device until the test result is obtained by the immuno-chromatographic measurement apparatus.

An immuno-chromatographic measurement apparatus disclosed in Japanese Unexamined Patent Publication No. 2009-133813 (hereinafter, Patent Document 2) carries out a testing process using data which is obtained by reading the color development state of the test line when a reaction completion time depending on the reagent has elapsed after the device is loaded. This apparatus carries out a preliminary testing process in the course of the measurement to determine a stage of progression of the reaction between the reagent and the test article injected in the device, and if it is determined that the reaction between the reagent and the test article has been completed, the last obtained result of the preliminary testing may be outputted as the final test result of this device. With this device, temporal change of the color development state and the test result can automatically be obtained after the sample solution is put on the device and until the end of the test, and time measurement by the user is not necessary. Therefore, the user can continue operation of putting the sample solution on other devices, etc.

The apparatus disclosed in Patent Document 2, however, is simple automation of the conventional method practiced by the user using a visual test kit (that is, in principle, determination of the test result is carried out when a reaction completion time determined for each reagent has elapsed; however, if it can be seen through visual observation that the reaction has apparently completed, the test result is determined before the reaction completion time elapses). Therefore, if the concentration of the test article in the sample solution is low or the reaction completion time determined for the reagent used is long, for example, it may take a considerably long time to obtain the test result. In particular, if the concentration of the test article in the sample solution is low, the color development state of the test line may not reach a predetermined value indicating a visually observable level, and an erroneous "negative (false-negative)" determination may be made.

In order to avoid such a situation, an amplifying solution may be put in advance on all the devices used in the test to amplify the color development state of the test line, or the amplifying solution may be put as appropriate depending on the state of progress of the test after a predetermined time to amplify the color development state of the test line and carry out the determination of the test result again. However, in the former case, the amplification step is carried out even when the test does not require the amplification step, and the time taken for obtaining the test result is increased. In addition, the amplifying solution is wasted. The latter case, after all, requires management and operation by the user for time measurement, and the user is interrupted by such operation.

As described above, although there are strong demands for a technique to provide a highly reliable test result in a simple and quick manner at the POCT sites, the conventional immuno-chromatographic measurement apparatuses have not succeeded in sufficiently responding to the demands.

SUMMARY OF THE INVENTION

In view of the above-described circumstances, the present invention is directed to providing a chromatographic measurement apparatus and a chromatographic measurement method for carrying out a test using an assay device, which allow providing a highly reliable test result in a simple and quick manner.

An aspect of the chromatographic measurement apparatus according to the invention is a chromatographic measurement apparatus for measuring a color development state of a testing area of an insoluble carrier having an label substance immobilized thereon to test a test article, the testing area including a test detection area where a material that binds specifically to the test article is immobilized and a control detection area used for determining an end of measurement, a sample solution possibly containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary.

The "testing area" herein refers to a predetermined area, such as an area including the detection areas (the test detection area and the control detection area), on the insoluble carrier.

The description "measuring a color development state of a testing area" refers, besides measuring the color development state of the detection areas, to measuring the color development state of the testing area other than the detection areas (i.e., an area forming the background of the detection areas). Measuring the color development state herein refers to obtaining optical information of the testing area, i.e., measuring optical density and chromaticity of the testing area, regardless of whether or not the detection areas have developed color.

The "optical density" herein is defined by Equation 1 below:

$$\text{Optical Density} = -\log_{10}(Ir/I) \qquad \text{Eq. 1,}$$

where I represents an intensity of incident light on the testing area of the assay device, and Ir represents an intensity of reflected light from the testing area.

The "chromaticity" herein refers to a value that quantitatively represents hue and saturation, and is calculated from an RGB luminance signal, which is obtained by reading the reflected light from the testing area with an image sensor.

The "determination of validity" of the test result herein refers to determining whether or not the test of the test article is progressing or has finished normally, or whether or not the test result is reliable. Based on the determination of validity, if the test result is reliable, the determining means outputs a "valid" determination, or if the test result is unreliable, the determining means outputs an "error" determination. Further, at the end of the test, the determining means outputs a determination as to whether the test result is positive or negative, together with the "valid" determination.

The "determination of necessity of amplification" of the test result herein refers to determining whether or not it is necessary to amplify the color development state.

To "amplify the color development state" herein means to amplify the value of the optical density, which may be accompanied by change of the chromaticity.

In the chromatographic measurement apparatus according to the invention, the determining means may determine in the determination of necessity of amplification that amplification is necessary if the optical density and the chromaticity of at least one of the test detection area and the control detection area have not reached a predetermined value, and the color development state amplified by the amplifying means may be measured to test the test article.

The "predetermined value" of the color development state, or of the optical density and the chromaticity herein refers to a value that is used as a criterion for the determination of necessity of amplification or the determination of validity by the determining means of the invention, and may be set as appropriate. For example, the predetermined value may be a "predetermined value indicating a visually observable level". The "predetermined value indicating a visually observable level" refers to that the optical density and the chromaticity of the color development state of each detection area are in a range where they are clearly distinguishable from the optical density and the chromaticity of the insoluble carrier forming the background (BG) with a normal human eye. The range of the optical density and the chromaticity clearly distinguishable with a normal human eye varies depending on the optical density and the chromaticity of the BG, and thus cannot be determined unambiguously. However, in general, when the BG is light, the optical density and the chromaticity of the color development state of each detection area are such that a density difference (a difference between the optical density of the color development state of each detection area and the optical density of the BG) is about 5 mOD (OD: Optical Density), and a color difference (a difference between the chromaticity of the color development state of each detection area and the chromaticity of the BG) is about 1 to 2.

The chromatographic measurement apparatus according to the invention may further include operation mode selecting means for allowing selection of an operation mode for causing the apparatus to carry out a predetermined operation.

In this case, the operation mode selecting means may include, as a selectable operation mode, an operation mode in which the measuring means measures the optical density and the chromaticity of the test detection area and the control detection area when a predetermined time has elapsed after the sample solution is put on the insoluble carrier, if the optical density and the chromaticity of all the detection areas have reached the predetermined value, the determining means determines in the determination of necessity of amplification that amplification is unnecessary and carries out the determination of validity of the test result of the test article without the amplification being carried out, or otherwise, the determining means determines in the determination of necessity of amplification that amplification is necessary, the amplifying means amplifies the color development state, and the determining means carries out the determination of validity of the test result of the test article after the amplification.

The chromatographic measurement apparatus according to the invention may further include specifying means for allowing, when there are two or more test detection areas, specification of apart of the test detection areas as a test detection area to be tested, and wherein the operation mode selecting means comprises, as a selectable operation mode, an operation mode in which the measuring means measures the optical density and the chromaticity of the test detection areas and the control detection area when a predetermined time has elapsed after the sample solution is put on the insoluble carrier, if the optical density and the chromaticity of the part of the test detection areas specified via the specifying means and the control detection area have reached the predetermined value, the determining means determines in the determination of necessity of amplification that amplification is unnecessary and carries out the determination of validity of the test result of the test article without the amplification being carried out, or otherwise, the determining means determines in the determination of necessity of amplification that amplification is necessary, the amplifying means amplifies the color development state, and the determining means carries out the determination of validity of the test result of the test article after the amplification.

The chromatographic measurement apparatus according to the invention may further include storing means for storing the test result of the test article. In this case, the storing means may store the test result and an identification mark associated with the test result, the identification mark indicating whether the test result was obtained before the amplification or after the amplification. The storing means may store the test result obtained before the predetermined time has elapsed if the determining means determines in the determination of validity that the test result of the test article is valid before the predetermined time has elapsed. The storing means may store the test result and an identification mark associated with the test result, the identification mark indicating that the test result was obtained before the predetermined time had elapsed.

The chromatographic measurement apparatus according to the invention may further include screen display means for displaying the test result and the identification mark.

The determining means may determine in the determination of validity that the test result is erroneous if the chromaticity of at least one of the test detection area and the control detection area before the amplification is different from a normal chromaticity before the amplification.

The determining means may determine in the determination of validity that the test result is erroneous if the chromaticity of at least one of the test detection area and the control detection area after the amplification is different from a normal chromaticity after the amplification.

The determining means may determine in the determination of validity that the test result is erroneous if the optical density and the chromaticity of the control detection area have reached the predetermined value immediately after the insoluble carrier is loaded in the apparatus.

The determining means may determine in the determination of validity that the test result is erroneous if a ratio of a value of the optical density after the amplification to a value the optical density before the amplification of at least one of the test detection area and the control detection area is smaller than a predetermined value.

The amplifying means may amplify the color development state by using an amplifying solution comprising a silver ion-containing compound and a reducing agent for reducing silver ions to deposit silver particles formed by reducing silver ions contained in the amplifying solution on the label substance.

An aspect of the chromatographic measurement method according to the invention is a chromatographic measurement method for measuring a color development state of a testing area of an insoluble carrier having an label substance immobilized thereon to test a test article, the testing area including a test detection area where a material that binds specifically to the test article is immobilized and a control detection area used for determining an end of measurement, a sample solution possibly containing the test article and the label substance for labeling the test article being developed on the insoluble carrier, the method comprising:

carrying out first determination as to whether or not amplification of the color development state is necessary based on optical density and chromaticity of the color development state measured when a predetermined time has elapsed after the sample solution is put on the insoluble carrier;

if it is determined in the first determination that amplification of the color development state is necessary since the optical density and the chromaticity of at least one of the test detection area and the control detection area have not reached a predetermined value, developing a cleaning solution and an amplifying solution on the insoluble carrier to clean the test detection area and the control detection area and amplify the color development state; and measuring optical density and chromaticity of the amplified color development state and carrying out second determination as to whether or not a test result is valid based on the optical density and the chromaticity of the amplified color development state.

In the chromatographic measurement method according to the invention, the predetermined time may be in the range from 5 to 20 minutes.

The second determination may be carried out within 1 to 20 minutes after the first determination.

An angle formed between a direction in which the sample solution is developed and a direction in which the cleaning solution is developed may be in the range from 45 to 170 degrees.

The label substance may be a metal colloid, and the metal colloid may be gold colloid.

The chromatographic measurement apparatus according to the invention includes the determining means for carrying out the determination of validity and the determination of necessity of amplification of the test result of the test article, and the amplifying means for developing the amplifying solution for amplifying the color development state according to the determination of necessity of amplification by the determining means. Therefore, in the apparatus of the invention, the color development state of the testing area is measured, and the determination of necessity of amplification (first determination) is carried out by the determining means based on the color development state. If it is determined that amplification is unnecessary in the determination of necessity of amplification, the determination of validity (second determination) is carried out based on the color development state. If it is determined that amplification is necessary in the determination of necessity of amplification, the color development state is amplified, and the determination of validity (second determination) is carried out based on the amplified color development state. As described above, the amplification step is carried out only when the amplification is necessary, thereby preventing increase of the test time, wasteful consumption of the amplifying solution and undue trouble of the user, which are otherwise caused by carrying out an unnecessary amplification step. Further, by amplifying the intensity of the signal of each detection area through the amplification of the color development state, a "false-negative" determination of the test result is prevented even when the concentration of the test article in the sample solution is low. As a result, a highly reliable test result can be provided in a simple and quick manner in a test using an assay device.

The chromatographic measurement method of the invention carries out the amplification step on the color development state according to the result of the determination of necessity of amplification (first determination), and carries out the determination of validity (second determination) based on the amplified color development state. Thus, increase of the test time, wasteful consumption of the amplifying solution and undue trouble of the user, which are otherwise caused by carrying out an unnecessary amplification step, as well as a "false-negative" determination of the test result can be prevented. As a result, a highly reliable test result can be provided in a simple and quick manner.

BRIEF DESCRIPTION OF THE DRAWINGS

FIG. 5A is a diagram for explaining a color development state and an example of determination of necessity of amplification and determination of validity, FIG. 5B is a diagram for explaining the color development state and an example of the determination of necessity of amplification and the determination of validity, FIG. 5C is a diagram for explaining the color development state and an example of the determination of necessity of the amplification and the determination of validity, FIG. 8 is a schematic diagram illustrating a test screen displayed on a screen displaying unit of the measurement apparatus.

DESCRIPTION OF THE PREFERRED EMBODIMENTS

Figure 1:
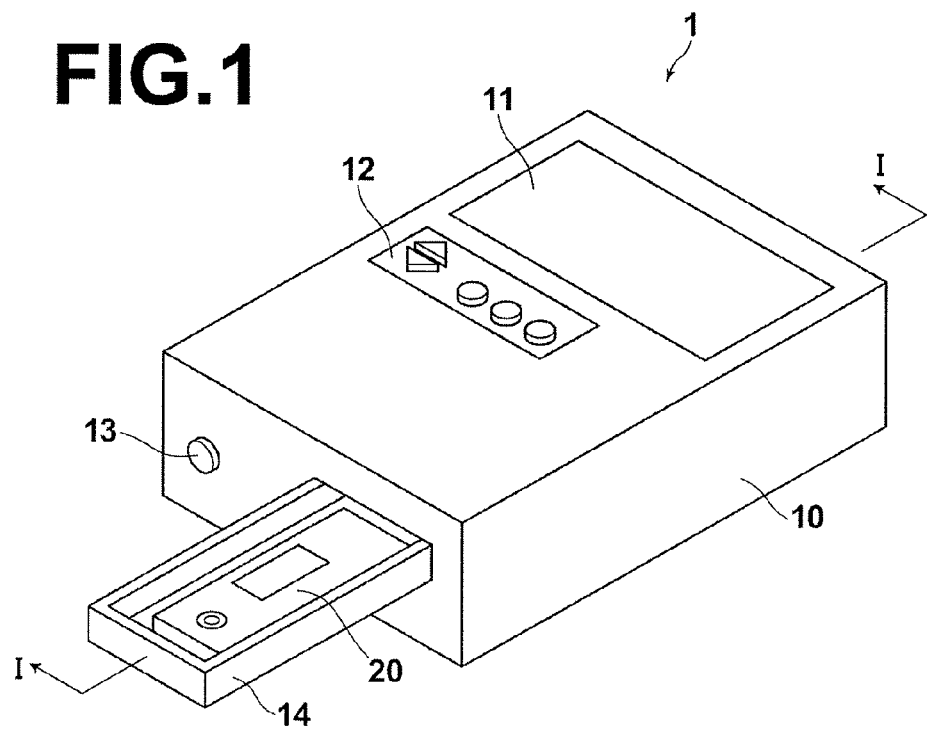
FIG. 1 is a schematic perspective view illustrating a chromatographic measurement apparatus according to a first embodiment.

Hereinafter, embodiments of the present invention will be described with reference to the drawings, which are not intended to limit the invention. For ease of visual recognition, elements shown in the drawings are not to scale.

First Embodiment
(Chromatographic Measurement Apparatus)

Figure 2:
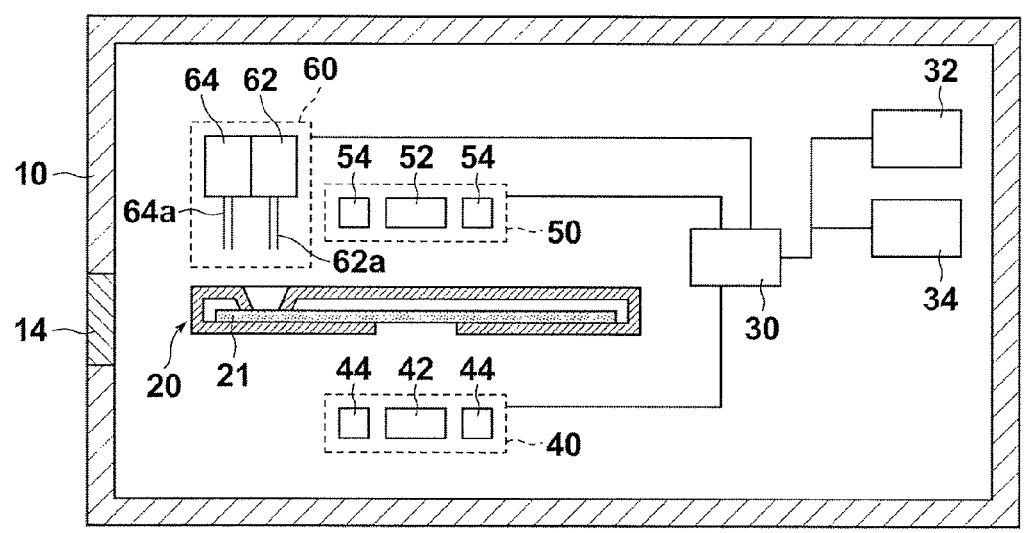
FIG. 2 is a schematic diagram illustrating the interior of the chromatographic measurement apparatus in cross-section taken along line I-I in FIG. 1.
Figure 3A:
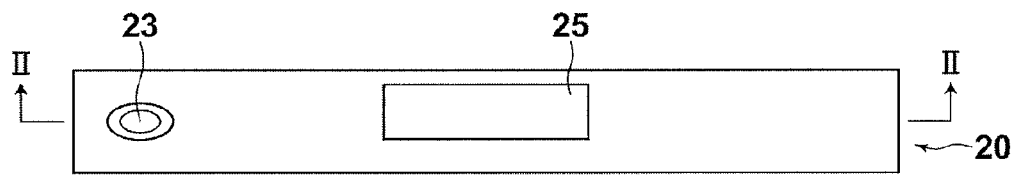
FIG. 3A is a schematic plan view illustrating an assay device to be loaded in the chromatographic measurement apparatus.
Figure 3B:
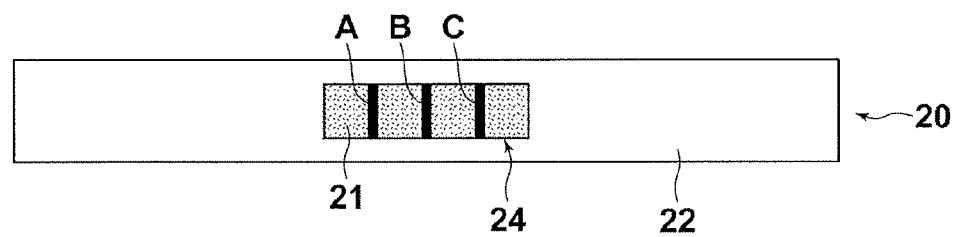
FIG. 3B is a schematic bottom view illustrating the assay device to be loaded in the chromatographic measurement apparatus.

First, the arrangement of a chromatographic measurement apparatus 1 according to a first embodiment is described. FIG. 1 is a schematic perspective view illustrating the appearance of the chromatographic measurement apparatus 1 of this embodiment, and FIG. 2 is a schematic diagram illustrating the interior of the chromatographic measurement apparatus 1 in cross-section taken along line I-I in FIG. 1, with an immuno-chromatographic device 20 loaded therein. FIGS. 3A and 3B are a schematic plan view and a schematic bottom view illustrating the appearance of the device 20, and FIG. 3C is a schematic sectional view taken along line II-II in FIG. 3A.

As shown in FIGS. 1 and 2, the chromatographic measurement apparatus 1 includes: a housing 10; a screen displaying unit 11 disposed at the surface of the housing 10; a menu operation section 12 for operating a menu displayed on the screen displaying unit 11; a power switch 13; a device loading section 14 for loading the device 20 in the apparatus. The chromatographic measurement apparatus 1 further includes in the interior thereof: a first measurement unit 40 and a second measurement unit 50 for obtaining information from the device 20; a determination unit 32 for carrying out a determination of validity and a determination of necessity of amplification of a test result of a test article based on the information obtained by the first measurement unit 40; an operation mode selection unit 34 for allowing selection of an operation mode to cause the apparatus to carry out a predetermined operation; an amplifying solution feeding unit 60 for developing an amplifying solution on an insoluble carrier 21 in the device 20; and a control unit 30 for controlling the first measurement unit 40, the second measurement unit 50, the determination unit 32, the operation mode selection unit 34 and the amplifying solution feeding unit 60.

Figure 3C:
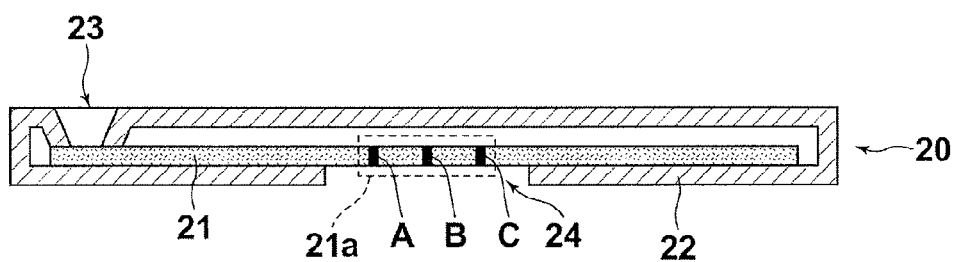
FIG. 3C is a schematic sectional view illustrating a cross-section of the assay device taken along line II-II in FIG. 3A.

Further, as shown in FIGS. 3A, 3B and 3C, the device 20 includes: the insoluble carrier 21 having two test lines (A and B) and a control line C; a device housing 22 for containing the insoluble carrier 21; a solution injection port 23 for injection of a reagent solution into the insoluble carrier 21; an observation window 24 for observation of a testing area 21a of the insoluble carrier 21 contained in the device housing 22; and an information display area 25 disposed at the surface of the device housing 22.

Now, the measurement apparatus 1 is described.
(Determination Unit)

The determination unit 32 of the chromatographic measurement apparatus 1 carries out, as a determining means according to the invention, the determination of validity and the determination of necessity of amplification of the test result of the test article based on a color development state of the testing area measured by the first measurement unit. The determination of validity is to determine whether states of progress of the test (such as a state of development of the solution, a state of capturing of the test article and a label substance on the test lines, a state of capturing of the label substance on the control line, etc.) are normal and the result to be obtained will be reliable, or whether or not the test has normally been completed and the result is reliable. In these cases, a "valid" determination is made when the test result will be or is reliable, or an "error" determination is made when the test result will be or is unreliable. The determination of necessity of amplification is to determine whether or not it is necessary to amplify the color development state of the testing area. If it is necessary, an "amplification necessary" determination is made, or if it is not necessary, an "amplification unnecessary" determination is made.

(Determination of Validity)

An example of the case where the "error" determination is made by the determination unit 32 while the test is progressing may be a case where it is determined that there is a possibility that the states of progress are not normal, and even if any test result will be obtained, the result may have low reliability. An example of the case where the states of progress of the test are not normal may be a case where the device 20 is reused and the control line has already developed color at an early stage of the test. If the "valid" determination is made by the determination unit 32 at the end stage of the test, the determination unit 32 also determines whether or not the test result is positive or negative. An example of the case where the "error" determination is made by the determination unit 32 at the end stage of the test may be a case where the states of progress are not normal and it is impossible to obtain a normal test result. Specific examples of the "error" determination that may be made at each stage will be described later.

(Determination of Necessity of Amplification)

An example of the case where the "amplification necessary" determination is made by the determination unit 32 may be a case where the concentration of the test article in the sample solution is low or where a reaction completion time of the test is long due to the nature of the reagent, etc., of the lines (the test lines and the control line), and it is estimated from the state of progress of the test that a considerable time will be taken for obtaining the test result if the test is continued without any modification. At which point of the states of progress the determination of necessity of amplification should be made may arbitrarily be set. The estimation as to whether or not it takes a considerable time can be achieved based on temporal changes of the color development state being measured. For example, the estimation may be achieved based on a rate of change of the optical density. An example of the case where the "amplification unnecessary" determination is made by the determination unit 32 may be a case where the concentration of the test article in the sample solution is high or where the reaction completion time of the test is short, and it is determined that the states of progress have already reached a level at which the test result can be obtained, or it is estimated that the test result can be obtained without taking a considerable time.

Timing to carry out the determination of validity and the determination of necessity of amplification in the progress of the test is not particularly limited. In the most basic test process, the determination of necessity of amplification and the determination of validity are carried out in this order when a predetermined time has elapsed after the sample solution is injected, and then, a final test result is obtained. The predetermined time may be set as appropriate by the user, such as a doctor, depending on the purpose of the test, reduction of the time taken for obtaining the test result, etc. For example, if the predetermined time is set shorter, the determination of necessity of amplification is carried out at an earlier stage to carry out the amplification step as necessary, thereby reducing the time taken for obtaining the test result. Further, as will be described later, in order to detect abnormality in the states of progress at an early stage of the test, another step of carrying out the determination of validity may be added to the basic test process before carrying out the determination of necessity of amplification, for example.

(Operation Mode Selection Unit)

The operation mode selection unit 34 has operation modes stored therein for causing the apparatus to carry out a predetermined operation. The stored operation modes are displayed as a menu on the screen displaying unit 11 via the control unit 30. The user of the measurement apparatus 1 can select one of the operation modes from the menu by operating the menu operation section 12. With this, the user can carry out a measurement operation that is suitable for the purpose of the test.

The operation mode stored in the operation mode selection unit 34 may, for example, be an operation mode (first operation mode) in which, when the predetermined time has elapsed after the sample solution is put on the insoluble carrier, a measuring means measures optical density and chromaticity of the test lines and the control line. If the optical density and the chromaticity have reached predetermined values for all the lines, a determining means makes the "amplification unnecessary" determination in the determination of necessity of amplification, and no amplification is carried out. Then, the determination of validity of the test result of the test article is carried out. Otherwise, the determining means makes the "amplification necessary" determination in the determination of necessity of amplification, and an amplifying means amplifies the color development state. After the amplification, the determining means carries out the determination of validity of the test result of the test article. In this operation mode, when a single device 20 has two or more test lines, highly reliable test can be achieved for all the test lines.

In the case where the device 20 have two or more test lines, and the measurement apparatus 1 includes a specifying means that allows the user to specify a part of the two or more test lines to be tested, another operation mode (second operation mode) may be stored in the operation mode selection unit 34. In this operation mode, for example, when the predetermined time has elapsed after the sample solution is put on the insoluble carrier, the measuring means measures the optical density and the chromaticity of the test lines and the control line. If the optical density and the chromaticity of the part of the test lines specified via the specifying means and the control line have reached predetermined values, the determining means makes the "amplification unnecessary" determination in the determination of necessity of amplification and no amplification is carried out. Then, the determination of validity of the test result of the test article is carried out. Otherwise, the determining means makes the "amplification necessary" determination in the determination of necessity of amplification, and the amplifying means amplifies the color development state. After the amplification, the determining means carries out the determination of validity of the test result of the test article. With this operation mode, wasteful test time can be reduced, and the test for the specified test line can efficiently be carried out.

(Measurement Unit)

The first measurement unit 40 serves as the measuring means according to the invention, which measures the color development state of the testing area 21a through the observation window 24 of the device 20 and obtains optical information of the testing area 21a. As shown in FIG. 2, the first measurement unit 40 includes an image sensor 42 and a light source 44. When the device 20 is loaded in the measurement apparatus 1, the image sensor 42 and the light source 44 are positioned below the device 20 and face to the observation window 24. Then, based on the optical information of the testing area 21a obtained by the first measurement unit 40, the optical density and the chromaticity are calculated as the color development state of the testing area 21a.

The image sensor 42 is formed, for example, by a linear array of photodiodes or an optical sensor, such as an area sensor, and generates an output corresponding to the luminance of the received light. A light-receiving area of the image sensor 42 is a zonal area extending in the longitudinal direction of the device 20. The light source 44 is, for example, a module including LEDs, and emits white light. The light source 44 may emit monochromatic light, for example, as long as the chromaticities before and after the amplification are distinguishable. If the light source 44 includes a plurality of modules, the modules may emit monochromatic light with different wavelengths. The light emitted from the light source 44 can illuminate along the longitudinal direction of the device 20.

The second measurement unit 50 applies illumination light to the information display area 25 of the device 20, and obtains information displayed on the information display area 25. The information display area 25 contains information about the test, which is displayed, for example, in the form of a hand-written text or a sticker attached on the information display area 25. The information about the test may include, for example, information about the patient from whom the test article was collected (such as name, age, sex, etc.) and information about the sample and reagent used in the test (such as names, or the like, of the test article, a cleaning solution, the amplifying solution, etc.) The method used to obtain the information is not particularly limited. The information may be obtained by capturing an image of the information display area 25 or by reading bar-code information, for example. As shown in FIG. 2, the second measurement unit 50 includes an image sensor 52 and a light source 54. When the device 20 is loaded in the measurement apparatus 1, the image sensor 52 and the light source 54 are positioned above the device 20 and face to the information display area 25. The information about the test obtained by the second measurement unit 50 and the test result are managed with being associated with each other. The details of the image sensor 52 and the light source 54 are the same as the image sensor 42 and the light source 44 described above.

(Optical Density)

The optical density is defined by Equation 1 below:

$$\text{Optical Density} = -\log_{10}(Ir/I) \qquad \text{Eq. 1,}$$

where I represents an intensity of incident light on the testing area of the assay device, and Ir represents an intensity of reflected light from the testing area.

(Chromaticity)

The chromaticity is a quantitative representation of hue and saturation, and is calculated from an RGB luminance signal read by the image sensor. The color system of the chromaticity may be the common CIE color system.

(Amplifying Solution Feeding Unit)

The amplifying solution feeding unit 60 includes: an amplifying solution reservoir 62 for storing an amplifying solution containing a silver ion-containing compound; an amplifying solution injection nozzle 62a for injecting the amplifying solution from the amplifying solution reservoir 62; a reducing agent reservoir 64 for storing a reducing agent used to reduce the silver ion contained in the amplifying solution; and a reducing agent injection nozzle 64a for injecting the reducing agent from the reducing agent reservoir 64. The amplifying solution feeding unit 60 is adapted to be capable of injecting the liquids stored in the amplifying solution reservoir 62 and the reducing agent reservoir 64 through the injection nozzles 62a and 64a, respectively, through the solution injection port 23 of the device 20 loaded in the apparatus 1. The liquids may be separately injected in turn or alternately through the respective injection nozzles or the two nozzles may be connected at the ends thereof and the liquids fed from the respective reservoirs may be simultaneously injected by driving the amplifying solution feeding unit 60 with a driving device, for example.

The arrangement of the amplifying solution feeding unit 60 is not limited to the above-described arrangement. For example, the solutions stored in the reservoirs may be the amplifying solution and the cleaning solution, for example, or only a single reservoir for storing the amplifying solution may be provided. Further, it is not necessary to provide the reservoirs storing the solutions inside the measurement apparatus 1. For example, the reservoirs may be provided outside the measurement apparatus (the housing 10), and the solutions may be injected through the solution injection port 23 by operating the injection nozzles.

(Chromatographic Measurement Method)

Next, a chromatographic measurement method according to the invention is described.

In the measurement method according to this embodiment, the device 20 including the insoluble carrier 21, which includes the test line where a material that binds specifically to the test article is immobilized, the control line for determining the end of measurement and an immobilized label substance, is provided. Then, a sample solution, which may contain the test article to be tested, is injected through the solution injection port 23 of the device 20. When a predetermined time has elapsed after the sample solution is put on the insoluble carrier 21, the optical density and the chromaticity of the testing area 21a are measured as the color development state. Based on the optical density and the chromaticity, the determination of necessity of amplification (first determination) is carried out. If the "amplification necessary" determination is made in the determination of necessity of amplification since the optical density and the chromaticity of at least one of the test lines (A and B) and the control line C have not reached the predetermined values, then, the reducing agent (in this embodiment, the reducing agent also serves as the cleaning solution) is developed on the insoluble carrier 21 to clean the test lines (A and B) and the control line C (a cleaning step), and the amplifying solution is developed on the insoluble carrier 21 to deposit silver particles, which are formed by reducing the silver ions, on the label substance to amplify the color development state (an amplifying step). Then, the optical density and the chromaticity in the amplified color development state are measured, and the determination of validity (second determination) is carried out based on the measured optical density and the chromaticity. Otherwise, the above-described amplification step (including the cleaning step and the amplifying step) is not carried out, and the determination of validity (second determination) is carried out based on the optical density and the chromaticity used to carry out the determination of necessity of amplification (first determination).

In the chromatographic measurement method according to the invention, the predetermined time may be 5 to 20 minutes. Further, the second determination may be carried out within 1 to 20 minutes after the first determination. With such time setting, the necessity of amplification can be determined in an early stage, and the test result can be provided more quickly.

An angle formed between a direction in which the sample solution is developed and a direction in which the cleaning solution is developed may be 45 to 170 degrees, and the insoluble carrier may be a porous carrier.

Figure 4A:
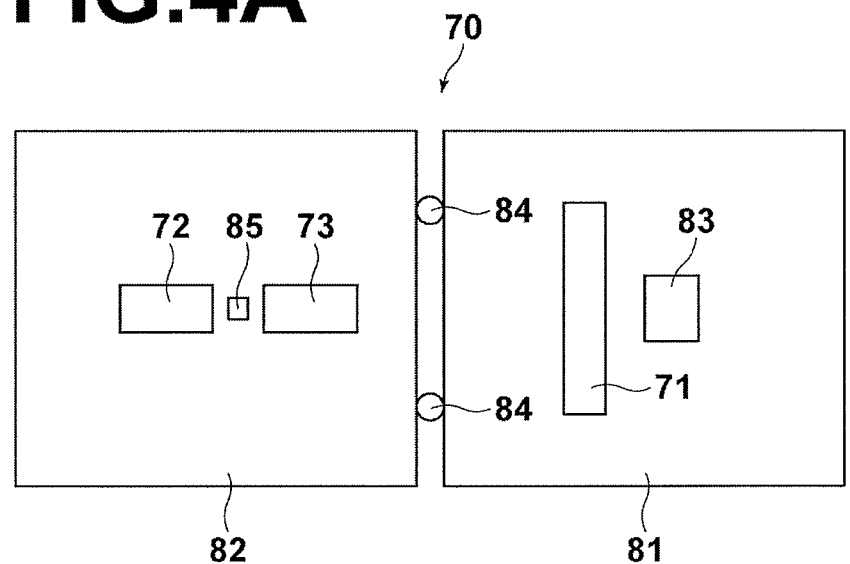
FIG. 4A is a schematic plan view illustrating another form of the assay device.
Figure 4B:
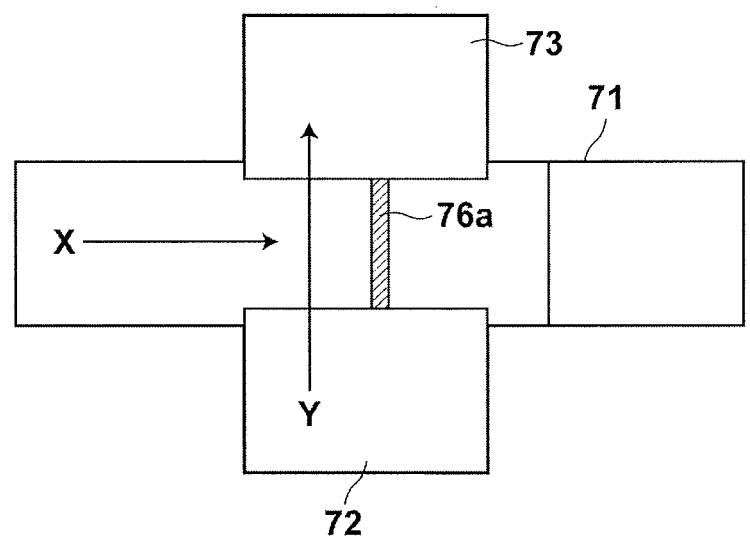
FIG. 4B is a schematic diagram illustrating a positional relationship between a liquid-feeding insoluble carrier and an absorbing insoluble carrier when the device shown in FIG. 4A is folded.

The angle formed between the direction in which the sample solution is developed and the direction in which the cleaning solution is developed can be adjusted using an immuno-chromatography kit 70 as shown in FIG. 4A, for example. The immuno-chromatography kit 70 includes a first device member 81 for retaining an immuno-chromatographic strip (insoluble carrier) 71, and a second device member 82 for retaining a liquid-feeding insoluble carrier 72 and an absorbing insoluble carrier 73, where the first device member 81 and the second device member 82 are connected via positioning members 84. The positioning members 84 are adapted to hold the first device member 81 and the second device member 82 together in a state where the immuno-chromatographic strip 71 does not contact the liquid-feeding insoluble carrier 72 and the absorbing insoluble carrier 73, and when the immuno-chromatography kit 70 is folded such that the first device member 81 and the second device member 82 face each other, the immuno-chromatographic strip 71 retained on the first device member 81 contacts the liquid-feeding insoluble carrier 72 and the absorbing insoluble carrier 73 retained on the second device member 82, as shown in FIG. 4B.

The first device member 81 includes an observation window 85 at a position corresponding to the center of the immuno-chromatographic strip 71 (a portion corresponding to a detection line 76a), so that the user can visually observe the detection line 76a through the observation window 85. The first device member 81 includes a liquid reservoir 83 to be filled with a liquid. The liquid reservoir 83 is adapted such that one end of the liquid-feeding insoluble carrier 72 is dipped in the liquid reservoir 83 when the first device member 81 and the second device member 82 are positioned and held in a position where the immuno-chromatographic strip 71 contact the liquid-feeding insoluble carrier 72 and the absorbing insoluble carrier 73.

Using the above-described kit, the sample solution put on the immuno-chromatographic strip 71 is fed in the direction of arrow X due to a capillary force. Thereafter, when the kit is folded, the liquid stored in the reservoir 83 is fed to the liquid-feeding insoluble carrier 72, the immuno-chromatographic strip 71 and the absorbing insoluble carrier 73 in this order in the direction of arrow Y. The above-mentioned angle can be adjusted by adjusting the positional relationship among the immuno-chromatographic strip 71, the liquid-feeding insoluble carrier 72 and the absorbing insoluble carrier 73, as appropriate.

Now, the measurement method is described.
(Sample Solution)

The sample solution which can be analyzed using the assay device of the invention is not particularly limited as long as the solution possibly contains the test article (for example, a physiologically active substance, such as a natural product, a toxin, a hormone or an agricultural chemical, or an environmental pollutant). Examples of the sample solution may include biological samples, in particular, body fluids (such as blood, blood serum, blood plasma, spinal fluid, tear, sweat, urine, pus, snivel and sputum), bodily wastes (such as feces), organ, tissue, mucosa and skin of an animal (in particular, human), a swab sample or a gargle fluid which possibly contain such a body fluid or a bodily waste, or a dilution of an animal or a plant itself or a dried body thereof diluted with a diluting fluid, which will be described later.

The sample solution may be used without any modification, or may be in the form of an extract obtained from the sample solution by using an appropriate extracting solvent, in the form of a diluting fluid obtained by diluting the extract with an appropriate diluting agent, or in the form of a condensate obtained by condensing the extract with an appropriate method.
(Label Substance)

The label substance usable in the invention is not particularly limited as long as the substance has a color and visually recognizable or can be tested through reaction, such as metal particles (or metal colloid), colored latex particles, an enzyme, or the like, which is commonly used in the immuno-chromatography. In the case where the signal is amplified by deposition of a metal on the label substance through a reducing reaction of ions of the metal with the label substance acting as the catalyst, the label substance may be metal particles in view of the catalyst activity.

The material of the metal particles may be a simple metal, a metal sulfide, a metal alloy, or a polymer particle label containing a metal. An average particle diameter of the particles (or colloid) may be in the range from 1 nm to 10 μm. The average particle diameter herein refers to an average of diameters of particles (the maximum diameter of each particle) measured using a transmission electron microscope (TEM). More particularly, the metal particles may be gold colloid, silver colloid, platinum colloid, iron colloid, aluminum hydroxide colloid, or a composite colloid thereof, and in particular, the metal particles may be gold colloid, silver colloid, platinum colloid, or a composite colloid thereof. In the case where gold colloid or silver colloid having an appropriate particle diameter is used, the gold colloid shows a red color and the silver colloid shows a yellow color, and thus high level of visual recognition is provided. When the gold colloid is used, the chromaticity of the label changes before and after the amplification step using the silver ion-containing compound (the gold colloid showing a red color is turned into black after the amplification by the reduced silver ions depositing on the particles of the gold colloid). This change of the color may be used for the "error" determination of the test, as will be described later. The average particle diameter of the metal colloid may be about 1 to 500 nm, or may optionally be 1 to 100 nm.
(Specific Binding Material)

The specific binding material is not particularly limited as long as it has an affinity for the test article. For example, if the test article is an antigen, the specific binding material may be an antibody to the antigen. If the test article is a protein, a metal ion or a low-molecular-weight organic compound, the specific binding material may be an aptamer to each of them. If the test article is a nucleic acid, such as DNA or RNA, the specific binding material may be a nucleic acid molecule, such as DNA or RNA, having a complementary sequence. If the test article is avidin, the specific binding material may be biotin. If the test article is a certain peptide, the specific binding material may be a complex that binds specifically to the peptide. With respect to the above-listed examples, the relationship between the specific binding material and the test article may be reversed. For example, if the test article is an antibody, the specific binding material may be an antigen to the antibody. Further, the specific binding material may be a compound, or the like, which contains at a part thereof a substance having an affinity for the test article, such as those described above.

As the antibody, specifically, an antiserum prepared from an animal serum immunized with the test article, an immune globulin fraction purified from the antiserum, a monoclonal antibody obtained through cell fusion using an animal spleen cell immunized with the test article, or a fragment thereof (for example, F(ab')2, Fab, Fab', or Fv) may be used. Preparation of the antibody is achieved using a common method.
(Signal Amplification of Label Substance)

In the case of assay which uses, as the label substance, a metal colloid label, a metal sulfide label, a metal alloy label, or a polymer particle label containing a metal, the signal of the metal label can be amplified. Specifically, after a composite of the test article and the label substance is formed, silver ions supplied from a silver-containing compound, such as an inorganic silver salt or an organic silver salt, and the reducing agent are brought into contact with each other to reduce the silver ions with the reducing agent to form the silver particles. Then, the silver particles deposit on the metal label with the metal label serving as a core. In this manner, the metal label is amplified, thereby achieving highly sensitive analysis of the test article.
(Insoluble Carrier)

The insoluble carrier 21 includes: a sample addition pad, where the sample solution is put; a label substance holding pad, where the label substance bindable to the test article is immobilized; a chromatographic carrier having the testing area, where the material that binds specifically to the test article is immobilized; and an absorbing pad, which absorbs the sample solution, or the like, fed thereto. The testing area includes two test lines, where different specific binding materials are immobilized, respectively. The number of the test lines is not limited to two, and one, or three or more test lines may be provided. In the case where the sample solution contains the two or more test articles, the two ore more test articles can simultaneously and efficiently be tested if two or more test lines are provided. The material forming the insoluble carrier 21 may be porous, and examples thereof may include nitrocellulose film, cellulose film, acetylcellulose film, polysulfone film, polyethersulfone film, nylon film, glass fiber, nonwoven fabric, fabric, or thread.

The chromatographic carrier includes the test lines, which are formed by immobilizing the specific binding materials to the test article, and optionally the control area. The specific binding material may be directly immobilized by physically or chemically binding the specific binding material to a part of the chromatographic carrier, or by physically or chemically binding the specific binding material to particles, such as latex particles, and trapping the particles at a part of the chromatographic carrier.

The label substance holding pad is prepared by preparing a suspension containing the label substance, applying the suspension to an appropriate pad (such as a glass fiber pad), and drying the pad. Thus, when the sample solution is injected into the insoluble carrier, the label substance is developed together with the test article and binds to the test article to flow to the testing area.

The sample addition pad receives the sample (such as the sample solution) put thereon, and also serves to filter insoluble particles, etc., in the sample. The sample addition pad may be subjected to a treatment to prevent nonspecific adsorption in advance in order to prevent nonspecific adsorption of the test article in the sample solution on the material of the sample addition pad during analysis, which may otherwise degrade accuracy of the analysis.

The absorbing pad physically absorbs the sample which has been added and chromatographically moved, and also serves to absorb and remove unreacted portions of the label substance, etc., which have not been insolubilized on the lines of the chromatographic carrier. The speed of the chromatographic movement of the added sample after the leading edge of the sample has reached the absorbing pad varies depending on the material and size of the absorbing pad. Therefore, an appropriate speed for the measurement of the test article can be set by selecting the material and size of the absorbing pad.
(Amplifying Solution)

The amplifying solution is a solution that is capable of amplifying the signal when a chemical contained therein is reacted by catalytic action of the label substance or the test article to form a compound that shows a color or produces luminescence, for example. For example, the amplifying solution may be a silver ion solution, which causes deposition of metal silver on a metal label through a physical phenomenon. More particularly, a so-called photographic developer, as described in literature in the art of photographic chemistry (for example, "Kaitei Shashin-kogaku no Kiso—Gin-en-shashin-hen (revised version of basic photographic engineering—silver-salt photography)" (edited by The Society of Photographic Science and Technology of Japan, published by Corona Publishing Co., Ltd.), "Shashin no Kagaku (photographic chemistry)" (Akira Sasai, published by Shashin-kogyo Shuppansha), "Saishin Shohou Handbook (the newest formulation handbook)" (Shin-ichi Kikuchi, et al., published by Amiko Shuppansha)). For example, in the case where the amplifying solution is a physical photographic developer containing a silver ion-containing compound, the silver ions in the amplifying solution are reduced by a silver ion reducing agent to deposit around the particles in the metal colloid, which form cores for the image development.

As another example, an enzyme reaction may be used. For example, a solution of a phenylenediamine compound and a naphthol compound, which form a dye through an action between a peroxidase label and hydrogen peroxide, may be used. As yet another example, a color-developing substrate for detecting horseradish peroxidase, as disclosed in K. Tanaka and Y. Miki, "Dyeing Using a $H_2O_2$-POD System", Rinsho-Kensa (clinical test), Vol. 41, No. 9, pp. 1020-1024, may be used. As still another example, a color-developing substrate disclosed in Japanese Unexamined Patent Publication No. 2009-156612 may be used. As yet another example, a system which uses a metal catalyst, such as platinum particles, in place of an enzyme may be used.

As an example using another enzyme, a system which uses alkaline phosphatase as the label and 5-bromo-4-chloro-3-indolyl-phosphate, disodium salt (BCIP) as the substrate to develop a color may be used. Although the above-described examples are color developing reactions, any combination of an enzyme and a substrate commonly used in enzyme immunoassay may be used. Further, the substrate may be a chemiluminescent substrate or a fluorescent substrate.
(Silver Ion-Containing Compound)

The silver ion-containing compound may be an organic silver salt, an inorganic silver salt, or a silver complex. The silver ion-containing compound may be one which is highly soluble in a solvent, such as water, and examples thereof may include silver nitrate, silver acetate, silver lactate, silver butyrate and silver thiosulfate, and in particular, silver nitrate. The silver complex may have water-soluble ligands, such as hydroxyl group or sulfonic group, and an example thereof is hydroxythioether silver. The content of the inorganic silver salt or the silver complex as an amount of silver may be 0.001 to 0.2 mole/$m^2$, or may optionally be 0.01 to 0.05 mole/$m^2$.
(Silver Ion Reducing Agent)

The silver ion reducing agent may be any of inorganic and organic materials or a mixture thereof as long as the agent can reduce the silver ions into silver.

Examples of the inorganic reducing agent may include reducing metal salts and reducing metal complex salts having a metal ion with a variable valence, such as $Fe^{2+}$, $V^{2+}$ or $Ti^{3+}$. When an inorganic reducing agent is used, it is necessary to complexate or reduce the oxidized ion to remove it or render it harmless. For example, with a system using $Fe^{2+}$ as the reducing agent, citric acid or EDTA may be used to complexate $Fe^{3+}$ in the form of an oxide to render it harmless. In the system of the invention, such an inorganic reducing agent may be used, and in particular, a metal salt of $Fe^{2+}$ may be used.
(Specific Examples of Determination of Necessity of Amplification, etc.)

Now, how the determination of necessity of amplification and the determination of validity are carried out based on the color development state of the testing area is described with reference to specific examples shown in FIGS. 5A to 5E.

FIGS. 5A to 5E are conceptual diagrams showing examples of the color development state of the testing area during a test after the sample solution is injected into the device 20 and the device 20 is loaded in the measurement apparatus 1. As shown in the drawings, the test process mainly includes a step before the amplification, a step of the determination of necessity of amplification, a step after the amplification and a step of the determination of validity. In these drawings, "A" indicates a test line (A line) for testing a test article A, "B" indicates a test line (B line) for testing a test article B, which is different from the test article A, and "C"

indicates a control line (C line) for indicating the end of the test (i.e., that the label substance has reached the C line). The insoluble carrier in these examples uses, as the label substance, gold colloid which has appropriately been treated. Therefore, the A line and the B line turn red when the test articles A and B are tested, and the C line turns red when the test ends regardless of the presence or absence of the test article. In the following description, it is assumed that the "predetermined value", which is a criterion for the determination of necessity of amplification and the determination of validity, is set to a "predetermined value indicating a visually observable level", and the determinations are carried out depending on whether or not the color development state on each line is visually observable.

During the test according to the invention, the amplification step is carried out only when it is determined to be necessary to amplify the color development state in the determination of necessity of amplification. Examples of the cases where it is determined to be necessary to amplify the color development state are shown in FIGS. 5A and 5B.

STEP 1 of cases 1 to 6 in FIG. 5A shows states of the testing area when a predetermined time (10 minutes) has elapsed after the device 20 was loaded. When 10 minutes have elapsed after the device 20 was loaded, the determination of necessity of amplification is carried out in STEP 2. In the stage of 10 minutes after, none of the color development states of the test lines of the cases 1 to 6 have reached the predetermined value indicating a visually observable level. Therefore, the "amplification necessary" determination is made in the determination of necessity of amplification for all the cases. This may be the case when, although each test line has developed color, the optical density of the developed color has not reached the predetermined value indicating the visually observable level, and the developed color may possibly be visually observable by amplifying the color development state. STEP 3 shows the color development states of the testing area of theses cases after the amplification. In STEP 4, the determination of validity is carried out based on the color development state after the amplification. It can be seen from the states in STEP 3 that the A line has developed color for the case 4, the B line has developed color for the case 5, and the A line and the B line have developed color for the case 6. Therefore, the "valid" determination is made in the determination of validity for the cases 4 to 6, and test results "A positive" for the case 4, "B positive" for the case 5, and "A and B positive" for the case 6 are obtained. For the cases 2 and 3, only the C line has developed color after the amplification, and therefore, the "valid" determination is made in the determination of validity, and a test result "negative" is obtained for each case. For the case 1, none of the lines (in particular, the C line) have developed color even after the amplification, and therefore the "error" determination is made in the determination of validity, assuming that the test has not been normally completed due to some errors.

STEP 1 of cases 7 to 12 in FIG. 5B also shows states of the testing area when a predetermined time (10 minutes) has elapsed after the device 20 was loaded. Similarly to the above-described cases shown in FIG. 5A, when 10 minutes have elapsed after the device 20 was loaded, the determination of necessity of amplification is carried out in STEP 2. In the stage of 10 minutes after, the color development state of at least one of the test lines has reached the predetermined value indicating the visually observable level in each of the cases 7 to 12, and the rest of the test lines and the C line have not reached the predetermined value indicating the visually observable level. Therefore, the "amplification necessary" determination is made in the determination of necessity of amplification for all the cases. This is because that the developed color may possibly be visually observable by amplifying the color development state. STEP 3 shows the color development states of the testing area of theses cases after the amplification. In STEP 4, the determination of validity is carried out based on the color development state after the amplification. Based on the states in STEP 3, the "valid" determination is made in the determination of validity for the cases 7 to 9, and test results "A positive" for the case 7, "B positive" for the case 8, and "A and B positive" for the case 9 are obtained. In contrast, for each of the cases 10 to 12, the C line in STEP 3 has not developed color and this indicates that the test has not been normally completed. Therefore, the "error" determination is made in the determination of validity.

Further, examples of the cases where it is determined to be unnecessary to amplify the color development state are shown in FIG. 5C.

FIG. 5C shows cases 13, 14, 16 and 17, where the test is carried out with applying the second operation mode described above. In the second operation mode, the determination of necessity of amplification is carried out only for a specified test line among the two or more test lines. For the cases 13 and 16, the A line is specified, and the A line and the C line have developed color of the visually observable level after the predetermined time (10 minutes) has elapsed. For the cases 14 and 17, the B line is specified, and the B line and the C line have developed color of the visually observable level after the predetermined time (10 minutes) has elapsed. Therefore, for theses cases, the "amplification unnecessary" determination is made in the determination of necessity of amplification regardless of the color development state of the other test line.

For the cases 15 and 18 in FIG. 5O, all the test lines and the C line have developed color of the visually observable level after or before the predetermined time (10 minutes) has elapsed. Therefore, for these cases, the "amplification unnecessary" determination is made in the determination of necessity of amplification (the first operation mode).

It should be noted that, as in the cases 16 to 18, if the color development state has already reached the level at which the purpose of the test is achieved before the predetermined time (10 minutes in this example) has elapsed, the determination of necessity of amplification may be carried out as appropriate before the predetermined timing to carry out the determination of necessity of amplification in order to reduce the test time.

In this manner, when the purpose of the test can be achieved without amplifying the color development state of the testing area, the "amplification unnecessary" determination is made as appropriate in the determination of necessity of amplification, thereby reducing the test time and use of the amplifying solution comparing to the case where the amplification step is always carried out.

The timing for carrying out the determination of validity according to the invention is not limited to when the final test result is obtained. For example, the determination of validity may be carried out immediately after the device 20 is loaded in the measurement apparatus 1. In this case, whether or not the test is normally progressing can be determined in the early stage of the test.

Figure 5D:
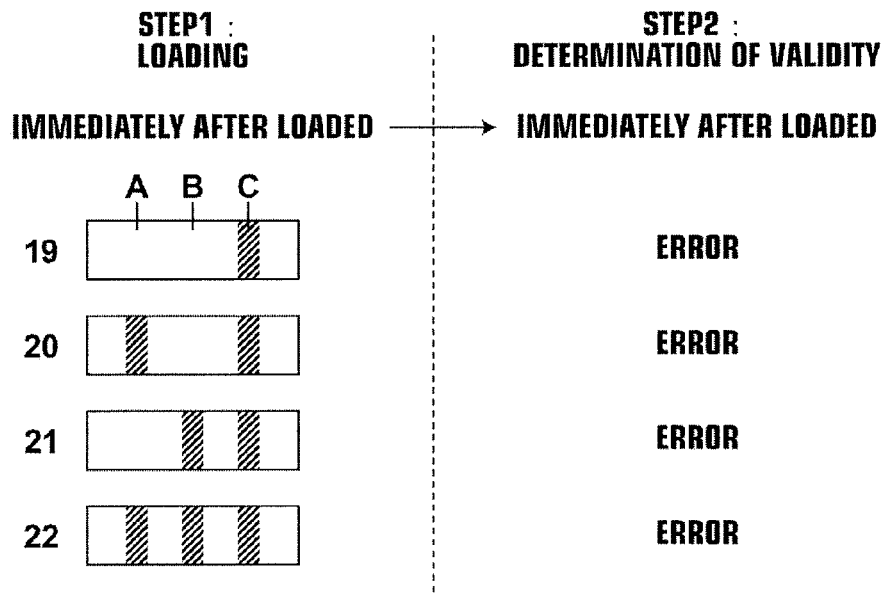
FIG. 5D is a diagram for explaining the color development state and an example of the determination of validity.

FIG. 5D shows cases 19 to 22 of states of the testing area immediately after the device 20 was loaded in the measurement apparatus 1. In these cases, the C line has already developed color immediately after the device 20 was loaded. In these cases, it is impossible to identify the time elapsed after the sample solution was put on the device 20 and before the device 20 was loaded. Therefore, the "error" determination is made in the determination of validity, assuming that the test result is not reliable.

Figure 5E:
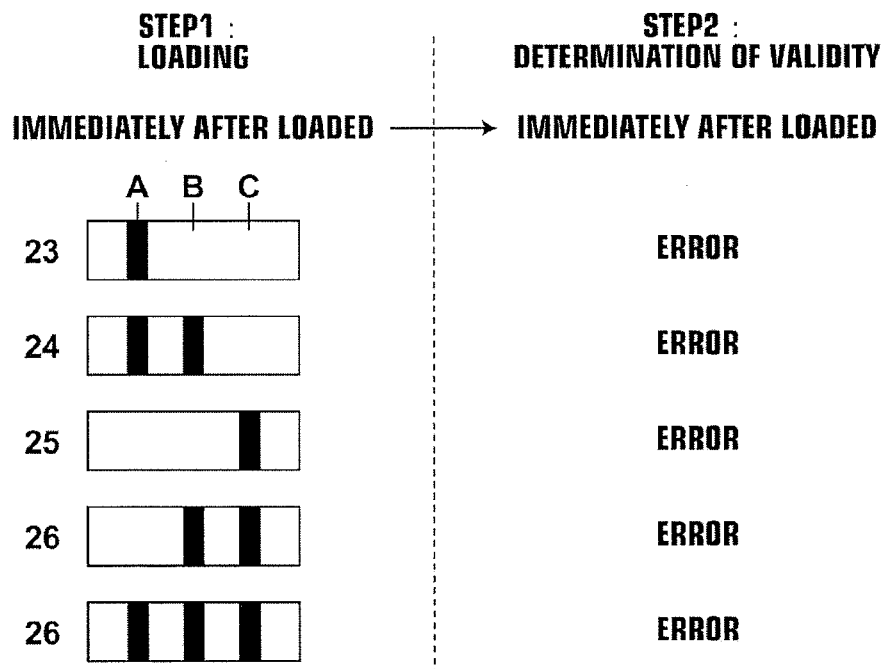
FIG. 5E is a diagram for explaining the color development state and an example of the determination of validity.

FIG. 5E also shows cases 23 to 27 of states of the testing area immediately after the device 20 was loaded in the measurement apparatus 1. In the cases 23 to 27, although the amplification of the color development state is not carried out, the chromaticity of the color development state of each line is at the same level as that after the amplification. In this case, it is possible that a once-used device is used again. Therefore, the "error" determination is made in the determination of validity, assuming that the test result is riot reliable. Information of reference chromaticities before and after the amplification may be set by the user in advance, or may be automatically set by the measurement apparatus 1 based on the information about the sample and the reagent used in the test, which is obtained from the information display area 25 of the device 20.

(Detailed Determination before and after Amplification Based on Optical Density and Chromaticity)

The determination of validity according to the invention may be carried out to make detailed determination as to whether or not the amplification step has been carried out normally based on the optical densities and the chromaticities of the testing area before and after the amplification. This can further increase reliability of the test result.

Figure 6A:
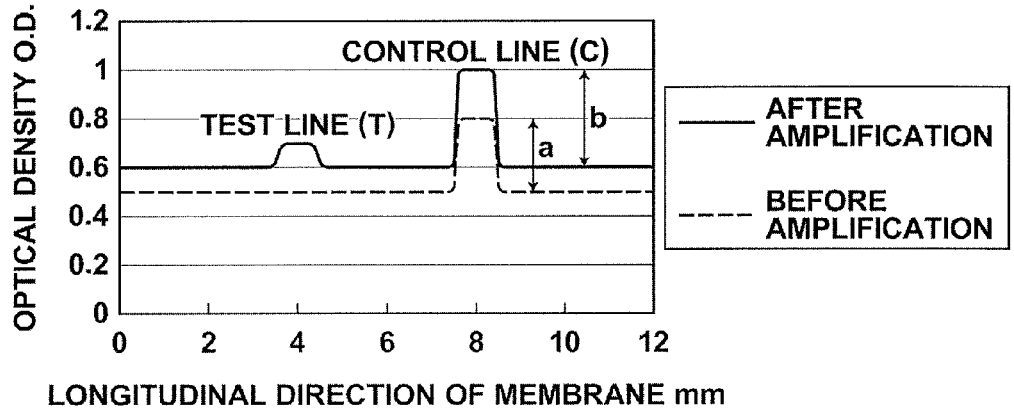
FIG. 6A is a diagram showing optical densities before and after amplification when an amplification step has been normally completed.

FIGS. 6A to 6D show the optical densities and the chromaticities of the testing area before and after the amplification, where the vertical axis of the graph corresponds to the optical density and the different types of lines correspond to the different types of chromaticities. FIG. 6A shows a case where the amplification step has been normally carried out and the optical density has been appropriately amplified, and the amplification with silver has changed the chromaticity from red (the developed color of the gold colloid) into black (the developed color of the silver particles). The symbols T and C in the graph indicate the test line (hereinafter, the T line) and the control line (hereinafter, the C line) of the insoluble carrier (membrane).

Figure 6B:
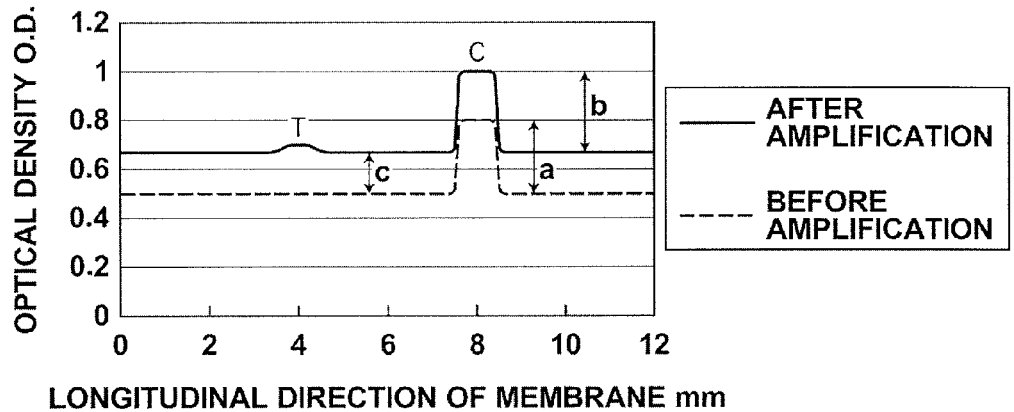
FIG. 6B is a diagram for explaining an example of a determination of erroneous end based on the optical densities before and after the amplification.

In the case shown in FIG. 6B, when a difference "a" between the optical density of the C line and the optical density of the background (BG) before the amplification is compared with a difference "b" between the optical density of the C line and the optical density of the BG after the amplification, the ratio of the density difference b to the density difference a is smaller than its prescribed value since a difference "c" between the optical densities of the BG before and after the amplification is larger than its prescribed value. In this case, the "error" determination is made in the determination of validity assuming that, although the amplifying step has been carried out normally to some extent, the cleaning step of the testing area has not been carried out normally.

Figure 6C:
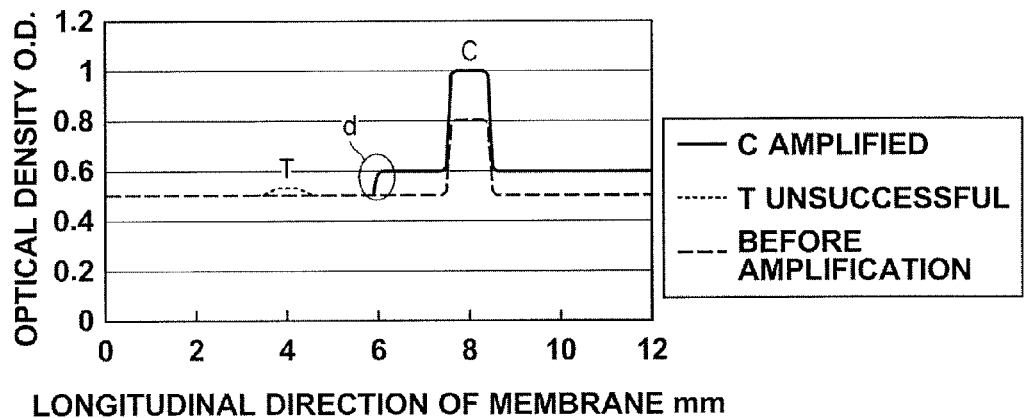
FIG. 6C is a diagram for explaining an example of the determination of erroneous end based on the optical densities before and after the amplification.

In the case shown FIG. 6C, although the optical density of the C line has normally been amplified, the optical density of the T line has not been amplified and the chromaticity after the amplification has not been changed into a normal chromaticity. Further, an unnatural level difference d of the optical density is generated in the BG between the T line and the C line. In this case, the "error" determination is made in the determination of validity assuming that, although the amplifying solution was fed from the right in the longitudinal direction of the membrane shown in FIG. 6C, a sufficient amount of the amplifying solution reached only to a part of the testing area.

Figure 6D:
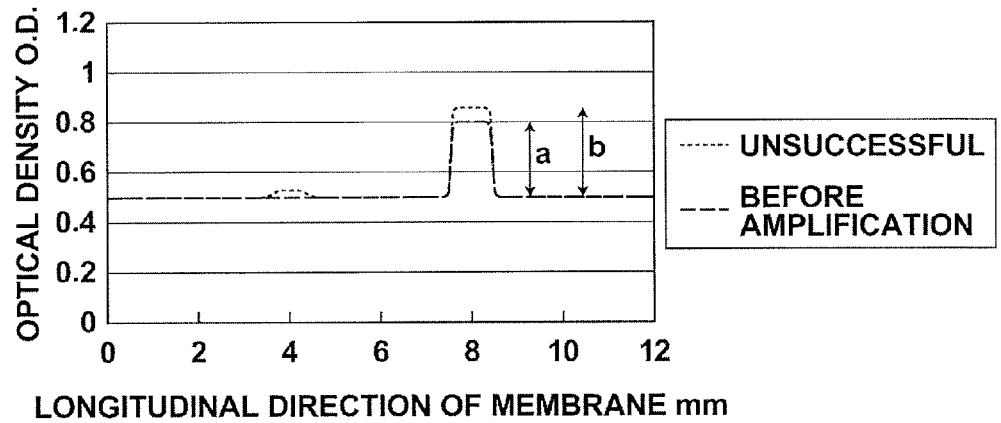
FIG. 6D is a diagram for explaining an example of the determination of erroneous end based on the optical densities before and after the amplification.

In the case shown FIG. 6D, the ratio of the density difference b to the density difference a is smaller than the prescribed value, and the chromaticity of each line after the amplification has not been changed into a normal chromaticity. In this case, the "error" determination is made in the determination of validity assuming that the amplifying step has not normally been carried out.

(Advantageous Effect of the Invention)

The measurement apparatus 1 of the invention includes determining means for carrying out the determination of validity and the determination of necessity of amplification of the test result of the test article, and amplifying means for developing the amplifying solution for amplifying the color development state according to the determination of necessity of amplification by the determining means. Thus, according to the apparatus of the invention, the color development state of the testing area is measured, and the determination of necessity of amplification (first determination) is carried out by the determining means based on the color development state. If the "amplification unnecessary" determination is made in the determination of necessity of amplification, the determination of validity (second determination) is carried out based on the color development state. If the "amplification necessary" determination is made in the determination of necessity of amplification, the color development state is amplified, and the determination of validity (second determination) is carried out based on the amplified color development state. By carrying out the amplification step only when it is necessary, as described above, increase of the test time, wasteful consumption of the amplifying solution and undue trouble of the user, which are otherwise caused by carrying out an unnecessary amplification step can be prevented. Further, by amplifying the intensity of the signal of each detection area (line) through the amplification of the color development state, a "false-negative" determination of the test result is prevented even when the concentration of the test article in the sample solution is low. As a result, a highly reliable test result can be provided in a simple and quick manner in a test using an assay device.

Further, the measurement apparatus 1 measures the chromaticity of the color development state, and determines the reliability of the test based on the chromaticity while the test is progressing and at the end of the test. Thus, a "false-negative" determination of the test result can be prevented.

The measurement method of the invention carries out the amplification step on the color development state according to the result of the determination of necessity of amplification (first determination), and then, carries out the determination of validity (second determination) based on the amplified color development state. Thus, increase of the test time, wasteful consumption of the amplifying solution and undue trouble of the user, which are otherwise caused by carrying out an unnecessary amplification step, as well as a "false-negative" determination of the test result can be prevented. As a result, a highly reliable test result can be provided in a simple and quick manner.

(Modification)

In the above-described embodiment, the amplification of the color development state is achieved by amplifying the label substance by reducing the silver ion-containing compound with the reducing agent. However, the method of amplification in the invention is not limited to the above-described method. The amplifying solution may be any solution that is capable of causing the amplification of the signal, such that a chemical contained in the amplifying solution is reacted by the catalytic action of the label substance or the test article to form a compound that shows a color or produces luminescence, for example. For example, the solution using an enzyme, as described above, may be used.

Although the above-described embodiment is described as the assay method relating to the immuno-chromatography, the assay method of the invention is not limited to that for the immuno-chromatography. The system may not use a so-called immune reaction. For example, the system may capture the test article with a nucleic acid, such as DNA or RNA, without using an antibody, or may capture the test article with a different type of small molecule, a peptide, a protein, a complex forming substance, or the like, which has an affinity for the test article.

Second Embodiment

Figure 7:
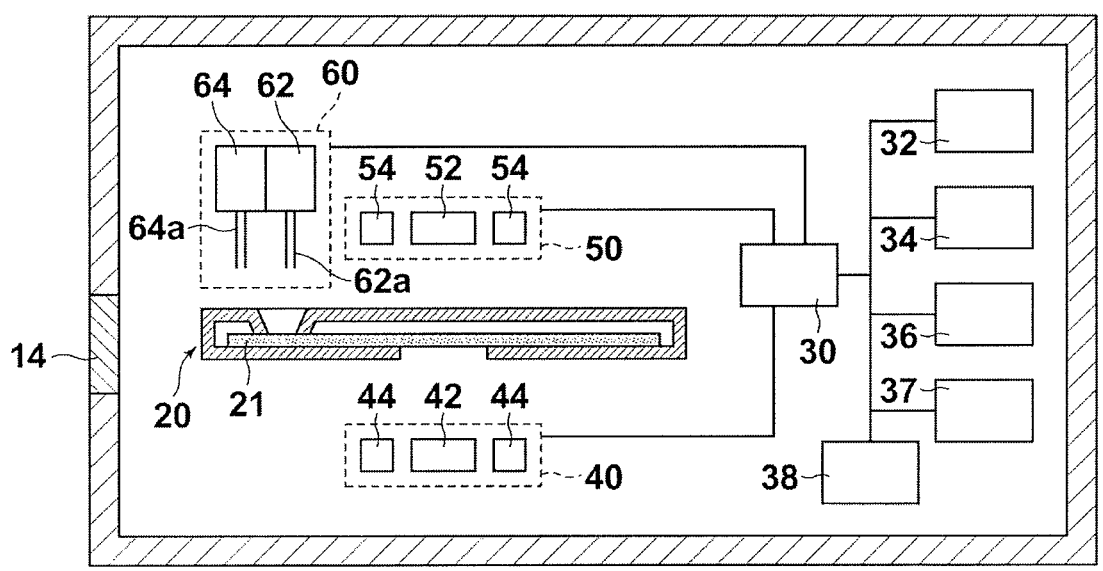
FIG. 7 is a schematic sectional view illustrating a chromatographic measurement apparatus according to a second embodiment.

FIG. 7 is a schematic sectional view illustrating a measurement apparatus 2 according to a second embodiment of the invention. The measurement apparatus 2 differs from the measurement apparatus of the first embodiment in that the information obtained by the image sensor (s) of the first measurement unit 40 and/or the second measurement unit 50 is displayed real-time on the screen displaying unit 11, and the information can be stored in the form of an image. The other points are the same as those of the first embodiment, and therefore are not described in detail unless otherwise necessary.

The measurement apparatus 2 includes, in addition to the components of the measurement apparatus 1: a storing unit 36 for storing information received from the measurement units 40 and 50; an image forming unit 37 for forming an image based on the above information; and an image processing unit 38 for applying image processing to the image formed by the image forming unit 37.

The storing unit 36 stores the information with adding time and date when the information is obtained to the information about the test obtained by the measurement unit 50, and classifying the information for each attribute and item in the form of a table. The attribute herein refers to the nature of the information, such as information about the patient from whom the test article was collected, information about the sample and reagent used in the test, etc. The item of the attribute includes, for example, name, age, sex, etc., for the former type of information, and names of the test article, the cleaning solution, the amplifying solution, etc., for the latter type of information. Further, the information of the testing area imaged by the image forming unit (the information obtained by the first measurement unit 40) can be stored with being associated with the above information in the form of a table.

The storing unit 36 stores the test result and an identification mark, which indicates whether the test result is obtained before or after the amplification, associated with the test result. Further, if the "valid" determination is made by the determining means 32 in the determination of validity of the test result of the test article before the predetermined time has elapsed after the sample solution is put on the insoluble carrier, the storing unit 36 can store the test result obtained before the predetermined time has elapsed. In this case, the storing unit 36 stores the test result and an identification mark, which indicates that the test result is obtained before the predetermined time has elapsed, associated with the test result. The test result stored as described above may optionally be displayed on the screen displaying unit 11. Since the test result is stored with being associated with the identification mark, the test result and the identification mark can simultaneously be displayed on the screen displaying unit, and this allows the user to easily understand how the test result was obtained.

The image forming unit 37 can form, besides a usual image, an image with a tag area embedded therein, an image with an electronic watermark embedded therein, or an image in the form of a two-dimensional code, according to setting. The file format of the image may be set as appropriate.

The image processing unit 38 applies image processing, such as noise reduction, shading correction, sharpness correction, lightness correction, contrast correction and hue conversion, to the formed image, as appropriate. Further, the image processing unit 38 may measure the color development state from the image for determination of the test result.

FIG. 8 shows an example of the information obtained by the measurement apparatus 2 displayed on the screen displaying unit 11 of the measurement apparatus 2. This example shows a test screen about an assay device which provides the test result in 15 minutes. As shown in the drawing, the test screen 90 includes: a test information display area 92, where the information about the test is displayed; a real-time display area 94, where a real-time image of the testing area obtained by the first measurement unit 40 is displayed; and a temporal image display area 96, where images of the testing area which have been previously obtained and stored in time series are displayed.

The test result determined from the image may also be displayed on the test screen 90.

The test information display area 92 includes the test item, the reference number of the test, the time and date of the test, the name of the patient to be tested, the elapsed time after the device is loaded, the image of the information display area 25 of the device obtained by the second measurement unit 50, etc. In addition, a text input area for allowing the user to input any text is displayed.

An image being displayed real-time on the real-time display area 94 can be saved at any point of time by using an intermediate image saving function. Further, the real-time display area 94 may display an image which has been subjected to the image processing by the image processing unit 38 to facilitate distinguishing between the lines and the BG. For example, the insoluble carrier typically has a yellowish color and is not a good BG for visual observation of the lines. By appropriately processing the BG color through the image processing, visual recognition of the lines can be improved.

On the temporal image display area 96, images saved after the device is loaded and until a predetermined time has elapsed are displayed in time series. For example, in the example shown in FIG. 8, a time of 13 minutes and 26 seconds has elapsed after the device was loaded, and images saved when 3 minutes, 5 minutes and 10 minutes have been elapsed are displayed in time series.

(Advantageous Effect of Second Embodiment)

As described above, in the measurement apparatus 2 of the second embodiment, the information obtained by the image sensor(s) of the first measurement unit 40 and/or the second measurement unit 50 is displayed real-time on the screen displaying unit 11, and the information can be stored in the form of an image. Conventional chromatographic measurement apparatuses have such a problem that, when the device is loaded in the apparatus, the apparatus becomes a so-called "black box", and it is impossible to learn the progress of the color developing reaction and prepare for the next action. According to the invention, the user can make real-time observation of the interior of the measurement apparatus 2. Thus, the user can learn the state of progress of the reaction easily, and can determine the end of the test easily. For example, when a developed color is observed after a shorter time than the reaction completion time that is determined depending on the reagent, the user can determine the end of the test at that point of time, and thus efficiency of the test can be increased.

Further, conventional visual observation test kits are not provided with means to keep the test result as an evidence and the time when the test result was determined. According to the invention, the temporal color development states and the color development state when the test result was determined can be kept as images and managed with an electronic health record. In addition, diagnosis can be carried out with presenting the images to the patient. Thus, admissibility of the test result as an evidence can be increased.

Further, by displaying the images obtained over time in time series, the images of the testing area obtained at different points of time can be directly compared with each other, and this allows more sensitive observation of changes of the developed color. If an abnormality is observed during the test, the cause of the abnormality, such as excess or deficiency of the amount of sample, can more easily be estimated, and the result in the form of the images can be kept as an evidence.

What is claimed is:

1. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:
    measuring means for measuring optical density and chromaticity as the color development state;
    determining means for carrying out determination of validity and determination of necessity of amplification of a test result of the test article based on the optical density and the chromaticity measured by the measuring means; and
    amplifying means for developing an amplifying solution for amplifying the color development state when it is determined in the determination of necessity of amplification that amplification is necessary, wherein
    the determining means determines in the determination of necessity of amplification that amplification is necessary if the optical density and the chromaticity of the test detection area or the control detection area have not reached a predetermined value, and
    the color development state amplified by the amplifying means is measured to test the test article.

2. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:
    measuring means for measuring optical density and chromaticity as the color development state;
    determining means for carrying out determination of validity and determination of necessity of amplification of a test result of the test article based on the optical density and the chromaticity measured by the measuring means;
    amplifying means for developing an amplifying solution for amplifying the color development state when it is determined in the determination of necessity of amplification that amplification is necessary;
    operation mode selecting means for allowing selection of an operation mode for causing the apparatus to carry out a predetermined operation,
    wherein the operation mode selecting means comprises, as a selectable operation mode, an operation mode in which the measuring means measures the optical density and the chromaticity of the test detection area and the control detection area when a predetermined time has elapsed after the sample solution is put on the insoluble carrier,
    if the optical density and the chromaticity of all the detection areas have reached the predetermined value, the determining means determines in the determination of necessity of amplification that amplification is unnecessary and carries out the determination of validity of the test result of the test article without the amplification being carried out, or
    otherwise, the determining means determines in the determination of necessity of amplification that amplification is necessary, the amplifying means amplifies the color development state, and the determining means carries out the determination of validity of the test result of the test article after the amplification.

3. The chromatographic measurement apparatus as claimed in claim 2, further comprising storing means for storing the test result of the test article.

4. The chromatographic measurement apparatus as claimed in claim 3, wherein the storing means stores the test result and an identification mark associated with the test result, the identification mark indicating whether the test result was obtained before the amplification or after the amplification.

5. The chromatographic measurement apparatus as claimed in claim 3, wherein the storing means stores the test result obtained before the predetermined time has elapsed if the determining means determines in the determination of validity that the test result of the test article is valid before the predetermined time has elapsed.

6. The chromatographic measurement apparatus as claimed in claim 5, wherein the storing means stores the test result and an identification mark associated with the test result, the identification mark indicating that the test result was obtained before the predetermined time had elapsed.

7. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:
    measuring means for measuring optical density and chromaticity as the color development state;
    determining means for carrying out determination of validity and determination of necessity of amplification of a test result of the test article based on the optical density and the chromaticity measured by the measuring means;
    amplifying means for developing an amplifying solution for amplifying the color development state when it is determined in the determination of necessity of amplification that amplification is necessary;
    operation mode selecting means for allowing selection of an operation mode for causing the apparatus to carry out a predetermined operation; and specifying means for allowing, when there are two or more test detection areas, specification of a part of the test detection areas as a test detection area to be tested, wherein the operation mode selecting means comprises, as a selectable operation mode, an operation mode in which the measuring means measures the optical density and the chromaticity of the test detection areas and the control detection area when a predetermined time has elapsed after the sample solution is put on the insoluble carrier, if the optical density and the chromaticity of the part of the test detection areas specified via the specifying means and the control detection area have reached the predetermined value, the determining means determines in the determination of necessity of amplification that amplification is unnecessary and carries out the determination of validity of the test result of the test article without the amplification being carried out, or otherwise, the determining means determines in the determination of necessity of amplification that amplification is necessary, the amplifying means amplifies the color development state, and the determining means carries out the determination of validity of the test result of the test article after the amplification.

8. The chromatographic measurement apparatus as claimed in claim 7, further comprising storing means for storing the test result of the test article.

9. The chromatographic measurement apparatus as claimed in claim 8, wherein the storing means stores the test result and an identification mark associated with the test result, the identification mark indicating whether the test result was obtained before the amplification or after the amplification.

10. The chromatographic measurement apparatus as claimed in claim 8, wherein the storing means stores the test result obtained before the predetermined time has elapsed if the determining means determines in the determination of validity that the test result of the test article is valid before the predetermined time has elapsed.

11. The chromatographic measurement apparatus as claimed in claim 10, wherein the storing means stores the test result and an identification mark associated with the test result, the identification mark indicating that the test result was obtained before the predetermined time had elapsed.

12. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary, wherein the determining means determines in the determination of validity that the test result is erroneous if the chromaticity of the test detection area or the control detection area before the amplification is different from a normal chromaticity before the amplification.

13. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary, wherein the determining means determines in the determination of validity that the test result is erroneous if the chromaticity of the test detection area or the control detection area after the amplification is different from a normal chromaticity after the amplification.

14. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary, wherein the determining means determines in the determination of validity that the test result is erroneous if the optical density and the chromaticity of the control detection area have reached a predetermined value immediately after the insoluble carrier is loaded in the apparatus.

15. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary, wherein the determining means determines in the determination of validity that the test result is erroneous if a ratio of a value of the optical density after the amplification to a value the optical density before the amplification of the test detection area or the control detection area is smaller than a predetermined value.

16. A chromatographic measurement apparatus for measuring a color development state of a testing area of an insoluble carrier having a label substance immobilized thereon to test a test article, the testing area including a test detection area where a material that binds specifically to the test article is immobilized and a control detection area used for determining an end of measurement, a sample solution containing the test article and the label substance for labeling the test article being developed on the insoluble carrier, the chromatographic measurement apparatus comprising:

measuring means for measuring optical density and chromaticity as the color development state;

determining means for carrying out determination of validity and determination of necessity of amplification of a test result of the test article based on the optical density and the chromaticity measured by the measuring means; and amplifying means for developing an amplifying solution for amplifying the color development state when it is determined in the determination of necessity of amplification that amplification is necessary, wherein the amplifying means amplifies the color development state by using an amplifying solution comprising a silver ion-containing compound and a reducing agent for reducing silver ions to deposit silver particles formed by reducing silver ions contained in the amplifying solution on the label substance.

* * * * *